(12) United States Patent
Berardesca et al.

(10) Patent No.: US 7,261,908 B2
(45) Date of Patent: Aug. 28, 2007

(54) COMPOSITION BASED ON NATURAL SUBSTANCES USEFUL IN THE MAINTENANCE OF THE CORRECT HYDRATION OF THE SKIN

(75) Inventors: Enzo Berardesca, Rome (IT); Gianfranco Merizzi, Turin (IT)

(73) Assignee: Medestea Internazionale SRL, Turin (IT)

( * ) Notice: Subject to any disclaimer, the term of this patent is extended or adjusted under 35 U.S.C. 154(b) by 155 days.

(21) Appl. No.: 10/930,630

(22) Filed: Aug. 31, 2004

(65) Prior Publication Data
US 2005/0089501 A1   Apr. 28, 2005

(30) Foreign Application Priority Data
Sep. 3, 2003   (IT) .......................... TO2003A0672

(51) Int. Cl.
*A61K 36/89*   (2006.01)
*A61K 36/00*   (2006.01)
*A61K 35/34*   (2006.01)

(52) U.S. Cl. ...................... 424/750; 424/548; 424/725

(58) Field of Classification Search ..................... None
See application file for complete search history.

(56) References Cited

U.S. PATENT DOCUMENTS

| | | | | |
|---|---|---|---|---|
| 5,804,594 A | * | 9/1998 | Murad | 514/474 |
| 2002/0012714 A1 | * | 1/2002 | Olson | 424/766 |
| 2002/0127256 A1 | * | 9/2002 | Murad | 424/401 |

FOREIGN PATENT DOCUMENTS

| | | | |
|---|---|---|---|
| FR | 2704390 | * | 11/1994 |
| JP | 11 113530 | | 4/1999 |
| WO | 01/85182 A2 | | 11/2001 |
| WO | 2004/034986 A2 | | 4/2004 |

* cited by examiner

Primary Examiner—Christopher R. Tate
(74) Attorney, Agent, or Firm—Merchant and Gould P.C.

(57) ABSTRACT

A composition based on natural substances, intended for oral administration, useful in the maintenance of the correct skin hydration and in the prevention and/or the treatment of the effects of skin ageing, in particular wrinkles, is described. The composition comprises in combination: ceramides from rice, fish cartilage hydrolysate, and one or more amino acids selected from L-proline, L-lysine, L-valine and L-cysteine.

12 Claims, No Drawings

COMPOSITION BASED ON NATURAL SUBSTANCES USEFUL IN THE MAINTENANCE OF THE CORRECT HYDRATION OF THE SKIN

The present invention relates to a composition based on natural substances, intended for oral administration, useful in the maintenance of the correct skin hydration and in the prevention and/or the treatment of the effects of skin aging, in particular wrinkles.

Hydration of the horny layer of the epidermis is an essential condition for keeping the skin smooth and soft, with no opacity or tendency for desquamation. Moreover, the maintenance of a correct skin hydration makes it possible to prevent and/or combat some of the effects of skin ageing, in particular wrinkles.

The term skin hydration is used to refer to the water present in the horny layer. This consists of broad, flat cells (the corneocytes) immersed in a lipid matrix, which gives rise to an elastic cushion. On average, the horny layer consists of about 10 layers of cells about 1 micrometer thick, whose size depends on age, sex and various factors, both internal and environmental. The cytoplasm of the corneocytes consists almost exclusively of a network of keratin bound together by large numbers of disulphide bonds.

This elastic cushion is covered with a thin layer made up of proteins other than keratin and of intercellular lipids, which are mainly made up of ceramides and also of fatty acids and cholesterol, both free and esterified with fatty acids. The synthesis of the intercellular barrier lipids is subject to homeostatic regulation, which can nonetheless prove insufficient if the skin is subjected for example to excessive use of detergents or comes into contact with mineral oils or organic solvents. Breakdown of the lipid barrier reveals itself in dry skin, readily subject to inflammatory reactions; the increased permeability of the horny layer predisposes the skin to atopic and contact dermatitis. Even in the absence of pathological signs, the homeostasis of the barrier is compromised by senescence and by aggressive agents often present in the environment (for example UV radiation and pollutants). Moreover, in old age, a reduced capacity to metabolise linoleic acid (LA) to gamma-linolenic acid (GLA), which has an important function in the homeostasis of the skin, is often observed. This deficiency is still more pronounced in atopic eczema.

To maintain its proper condition, the horny layer must contain water to at least 10% of its own weight. This water content is determined by the interaction of 3 factors:

the influx of water from the deep layers of the skin
evaporation at the body surface
the ability of the horny layer to retain water.

The loss of water by evaporation is contained by the intercellular lipid barrier, whose efficacy depends mainly on the quality and quantity of the polar lipids; among these, the ceramides predominate. The lipids, as well as having a sealing function (due to the hydro-phobic region of the double lipid layer) are also capable of stably binding water in the polar portion of the molecule. The ability of the skin to retain water is also increased by the so-called NMF (Natural Moisturizing Factors), described for the first time in 1959: these are water-soluble substances contained in the corneocyte, in which they represent about 10% of the dry weight. Among these, free amino acids (40% of the total; mainly serine, but also alanine, arginine, valine and proline), pyrrolidone-carboxylic acid (12%), urea (8%), sugars, lactic acid and inorganic ions have been identified. It is thought that the free amino acids may derive from a protein, known as filaggrin, which is dephosphorylated and hydrolysed during the maturation of the corneocyte.

The prevention and treatment of skin dehydration phenomena nowadays is essentially based on the use of compositions for topical application, for example LA and/or GLA or components of the NMF.

The present invention now makes available a composition active by the systemic route, capable of contributing to the maintenance of the correct skin hydration and hence of preventing or combating the effects of skin ageing, in particular wrinkles.

Thus the object of the invention is a composition based on natural substances, useful in the treatments mentioned above, characterized in that it comprises in combination:

ceramides in the form of extract of *Oryza sativa*,
fish cartilage hydrolysate, and
one or more amino acids selected from L-proline, L-lysine, L-valine and L-cysteine.

In particular, the extract of rice (*Oryza sativa*) is rich in ceramides, in other words lipids in which sphyngosine (a long-chain aliphatic amino alcohol) is bound to a molecule of fatty acid by an amide linkage. Clinical studies have demonstrated that the resistance of the cutaneous barrier to external agents diminishes with increasing age, in parallel with the diminution in the ceramides content. The hydrating effect of the ceramides has also been demonstrated; these are absorbed along the digestive tract and via the blood stream reach the horny layer where they improve the hydration and the barrier effect of the skin.

For the preparation of the composition of the invention, standardised, commercially available extracts of rice can be used.

The fish cartilage hydrolysate used in the context of the invention contains as the active principle chondroitin sulphate which consists of a mixture of acidic mucopolysaccharides, formed from a linear repetitive unit containing various sulphate groups. The basic units are made up of N-acetyl-galactosamine and glucuronic acid.

In a particularly preferred embodiment of the invention, the fish cartilage hydrolysate is a ray cartilage hydrolysate.

For the preparation of the composition of the invention, standardised, commercially available fish cartilage hydrolysates can be used.

The amino acids used in the composition of the invention, as mentioned above, form part of the NMF, increasing the hygroscopicity of the horny layer of the epidermis and hence its ability to retain water. These components are also readily available commercially.

The trials performed by the applicant have made it possible to confirm that the combination of the above-mentioned active principles exerts an effective action in the maintenance of the correct skin hydration and in the prevention and/or in the cosmetic and/or therapeutic treatment of the effects of skin ageing. The composition of the invention can thus be used for the preparation of a cosmetic product, a food supplement or a medicament for the above-mentioned treatments.

In a preferred embodiment, the composition of the invention can also contain active principles selected from eicosapentaenoic acid (EPA), docahexaenoic acid (DRA), γ-linolenic acid and mixtures thereof. As the source of eicosapentaenoic acid (EPA) and docahexaenoic acid (DHA) the use of fish oil and/or vegetable oil rich in DHA derived from microalgae is preferable. The γ-linolenic acid is preferably introduced into the composition through the use of borage oil. As an alternative to or in combination with the borage oil it is possible to use Evening Primrose (oenothera) oil.

One or more antioxidants, particularly vitamin E, bioflavonoids and lycopene, can also be included in the composition of the invention.

The composition according to the invention is formulated in suitable form for oral administration, such as in particular soft- or hard-shelled gelatine capsules, tablets, pills, elixir, suspensions or syrups.

The administration forms can comprise pharmaceutically acceptable excipients and/or binders and/or vehicles, in particular lecithin, fatty acid mono- and diglycerides, wheat germ oil.

In a preferred embodiment, the composition of the invention is in a dosage form for oral administration designed for the administration of:

from 4 to 80 mg/day of rice ceramides,
from 100 to 1000 mg/day of fish cartilage hydrolysate, and
from 20 to 200 mg/day of one or more amino acids selected from L-proline, L-lysine, L-valine and L-cysteine.

Such oral dosage form can be designed for the administration of the daily dosages indicated above in a single daily administration or in several successive daily administrations.

In another preferred embodiment, the composition is in a dosage form for oral administration comprising:

a base mixture as described above, containing rice ceramides, fish cartilage hydrolysate and one or more amino acids selected from L-proline, L-lysine, L-valine and L-cysteine;
one or more oils selected from fish oil, borage oil, Evening Primrose (oenothera) oil and vegetable oil rich in DHA derived from microalgae;
one or more antioxidants selected from vitamin E, bioflavonoids and lycopene; and
pharmaceutically acceptable excipients and/or binders and/or vehicles, wherein the base mixture is present in a quantity from 30 to 60% by weight of the total weight of the oral dosage form.

The assessment of the efficacy of the composition according to the invention was carried out by means of a study performed on subjects of female sex, free from cutaneous and/or systemic pathologies.

Capsules with a soft gelatine envelope were used, which contained:

rice ceramides: 14 mg/cap
ray cartilage hydrolysate: 150 mg/cap
L-proline: 40 mg/cap
L-lysine base: 40 mg/cap
L-valine: 40 mg/cap
L-cysteine base: 20 mg/cap
concentrated natural tocopherols: 25 mg/cap
lycopene: 10 mg/cap
borage oil: 60 mg/cap
fish oil: 180 mg/cap
wheat germ oil: 127 mg/cap
soya lecithin: 7 mg/cap
glyceryl monostearate: 17 mg/cap The experiment was performed on a total of 32 subjects, 16 of whom were treated with the product under test and 16 with a placebo. The daily dosage was 2 caps (morning and evening).

The experiment was performed for a total of 40 days, with an intermediate visit after 20 days.

During the visits, the subjects in the experiment were subjected to two types of instrument evaluation: evaluation of the skin hydration by corneometry and analysis of the image of the face by Visioscan which, through processing of the parameters shown in the notes to Table 2, makes it possible to obtain information both on the skin hydration and on the fine structure of the skin.

Further, the subjects were asked to express a judgement, with a number from 0 to 10, on the following parameters: hydration, tension, desquamation, elasticity, make-up, colour, tone and sebum.

The results obtained are illustrated in Tables 1 (corneometry), 2 (Visioscan) and 3 (Self-assessment).

TABLE 1

Corneometry

| Product according to the invention | | | | Placebo | | | |
|---|---|---|---|---|---|---|---|
| Basal | Intermediate | Final | p | Basal | Intermediate | Final | p |
| 55.86 | 58.05 | 72.47 | $p < 0.05$ | 59.64 | 60.53 | 59.33 | $p > 0.05$ |

TABLE 2

Visioscan

| Product according to the invention | | | | Placebo | | | |
|---|---|---|---|---|---|---|---|
| Basal | Intermediate | Final | p | Basal | Intermediate | Final | p |
| Volume | | | | | | | |
| 39.37 | 39.62 | 29.93 | $p < 0.05$ | 37.62 | 37.85 | 36.56 | $p > 0.05$ |
| Surface | | | | | | | |
| 3.65 | 3.38 | 2.83 | $p < 0.05$ | 3.11 | 3.26 | 3.01 | $p > 0.05$ |
| NRJ | | | | | | | |
| 0.080 | 0.091 | 0.120 | $p < 0.05$ | 0.105 | 0.156 | 0.105 | $p > 0.05$ |

TABLE 2-continued

Visioscan

| Product according to the invention | | | | Placebo | | | |
|---|---|---|---|---|---|---|---|
| Basal | Intermediate | Final | p | Basal | Intermediate | Final | p |
| Contrast | | | | | | | |
| 0.608 | 0.604 | 0.391 | $p < 0.05$ | 0.51 | 0.48 | 0.48 | $p > 0.05$ |
| Variance | | | | | | | |
| 2.70 | 2.63 | 2.01 | $p < 0.05$ | 2.27 | 2.41 | 2.25 | $p > 0.05$ |
| Sesc | | | | | | | |
| 0.48 | 0.45 | 0.20 | $p < 0.05$ | 0.54 | 0.54 | 0.50 | $p > 0.05$ |
| R1 | | | | | | | |
| 45.68 | 44.06 | 35.12 | $p < 0.05$ | 39.68 | 38.87 | 37.81 | $p > 0.05$ |
| R2 | | | | | | | |
| 39.93 | 37.18 | 29.75 | $p < 0.05$ | 34.37 | 33.75 | 33.56 | $p > 0.05$ |
| R3 | | | | | | | |
| 30.31 | 27.35 | 22.12 | $p < 0.05$ | 25.25 | 26.81 | 25.87 | $p > 0.05$ |
| R4 | | | | | | | |
| 24.81 | 24.62 | 17.93 | $p < 0.05$ | 22.56 | 21.68 | 21.25 | $p > 0.05$ |
| R5 | | | | | | | |
| 6.56 | 6.18 | 4.81 | $p < 0.05$ | 5.37 | 5.68 | 5.43 | $p > 0.05$ |
| Desq Index | | | | | | | |
| 25.14 | 26.07 | 24.19 | $p > 0.05$ | 26.97 | 25.24 | 27.06 | $p > 0.05$ |

Volume = depth of the microrelief;
Surface = smoothness;
NRJ = homogeneity of image;
Variance = microwrinkliness;
Sesc = hydration of horny layer;
R1-R5 = wrinkliness;
Desq Index = desquamation index

TABLE 3

Self-assessment

| Product according to the invention | | Placebo | | Inv. vs placebo | Inv. vs placebo |
|---|---|---|---|---|---|
| 20 days | 40 days | 20 days | 40 days | 20 days | 40 days |
| Hydration | | | | | |
| 7.2 | 7.8 | 6.2 | 6.1 | $p < 0.05$ | $p < 0.001$ |
| Tension | | | | | |
| 7.2 | 8 | 5.8 | 6.5 | $p < 0.05$ | $p < 0.001$ |
| Desquamation | | | | | |
| 7.1 | 7.8 | 6 | 6.3 | $p < 0.05$ | $p < 0.001$ |
| Elasticity | | | | | |
| 6.9 | 7.9 | 6 | 6.5 | $p < 0.05$ | $p < 0.001$ |
| Make-up | | | | | |
| 6.9 | 7.5 | 6.2 | 6.3 | $p < 0.05$ | $p < 0.001$ |
| Colour | | | | | |
| 7 | 7.9 | 6.4 | 6.6 | $p > 0.05$ | $p < 0.001$ |
| Tone | | | | | |
| 6.9 | 8.1 | 5.9 | 6.2 | $p < 0.05$ | $p < 0.001$ |
| Sebum | | | | | |
| 6.5 | 7.8 | 5.8 | 6.2 | $p < 0.05$ | $p < 0.001$ |

While the subjects treated with placebo did not display significant changes in the skin hydration, in the group treated with the composition of the invention a significant increase in skin hydration as measured by corneometry was recorded.

Moreover, analysis of the image of the face with the Visioscan showed a decrease in the depth of the microrelief, of the microwrinkliness, of the wrinkliness and of the desquamation index, and a concomitant increase in the smoothness and the homogeneity of the skin and in the hydration of the horny layer.

These instrument results indicate that the combination of the active principles characteristic of the composition of the invention exerts an effective hydration action on the skin which is also reflected in an improvement of the parameters correlated with the fine structure of the skin.

The instrument results obtained are moreover confirmed in the self-assessment test.

What is claimed is:

1. Composition based on natural substances, useful in the maintenance of the correct skin hydration and in the treatment of the effects of skin ageing comprising in combination: ceramides in the form of extract of Oryza sativa, fish cartilage hydrolysate, and one or more amino acids selected from L-proline, L-lysine, L-valine and L-cysteine, whereby the composition is in a dosage form for oral administration, and wherein the dosage form is designed for the oral administration of: from 4 to 80 mg/day of said ceramides, from 100 to 1000 mg/day of said fish cartilage hydrolysate, and from 20 to 200 mg/day of said one or more amino acids.

2. Composition according to claim 1, wherein the fish cartilage hydrolysate is ray cartilage hydrolysate.

3. Composition according to claim 1, further comprising one or more oils selected from fish oil, borage oil, Evening Primrose (oenothera) oil and vegetable oil rich in DHA derived from microalgae.

4. Composition according to claim 1, further comprising an antioxidant selected from vitamin E, bioflavonoids, lycopene and mixtures thereof.

5. Composition according to claim 1, further comprising pharmaceutically acceptable excipients and/or binders and/or vehicles.

6. Composition according to claim 1, which is in an oral dosage form comprising: a base mixture containing the ingredients cited in claim 1, one or more oils selected from fish oil, borage oil, Evening Primrose (oenothera) oil and oil rich in DHA derived from microalgae; one or more antioxidants selected from vitamin E, bioflavonoids and lycopene, and pharmaceutically acceptable excipients and/or binders and/or vehicles, wherein said base mixture is present in a quantity from 30 to 60% by weight of the total weight of the oral dosage form.

7. Composition according to claim 1, wherein the effects of skin aging that are treated are skin wrinkles.

8. A method for maintenance of correct skin hydration comprising administering an oral composition, food supplement, or medicament comprising the composition of claim 1.

9. A method for therapeutic treatment of the effects of skin aging comprising administering an oral composition, food supplement, or medicament comprising the composition of claim 1.

10. The method of claim 9 wherein the effects of skin aging are skin wrinkles.

11. A method for maintenance of correct skin hydration comprising administering an oral composition, food supplement, or medicament comprising the composition of claim 1.

12. A method for therapeutic treatment of the effects of skin aging comprising administering an oral composition, food supplement, or medicament comprising the composition of claim 1.

* * * * *